US006465718B1

(12) United States Patent
Inze et al.

(10) Patent No.: US 6,465,718 B1
(45) Date of Patent: Oct. 15, 2002

(54) METHOD AND MEANS FOR MODULATING PLANT CELL CYCLE PROTEINS AND THEIR USE IN PLANT CELL GROWTH CONTROL

(75) Inventors: Dirk Inze, Moorsel-Aalst; Gerda Segers, Ghent; Lieven De Veylder, Aalst; Vladimir Mironov, Ghent, all of (BE)

(73) Assignee: CropDesign N.V., Ghent (BE)

( * ) Notice: Subject to any disclaimer, the term of this patent is extended or adjusted under 35 U.S.C. 154(b) by 0 days.

(21) Appl. No.: 09/381,150
(22) PCT Filed: Mar. 13, 1998
(86) PCT No.: PCT/EP98/01522
§ 371 (c)(1), (2), (4) Date: Mar. 13, 2000
(87) PCT Pub. No.: WO98/41642
PCT Pub. Date: Sep. 24, 1998

(30) Foreign Application Priority Data

Mar. 14, 1997 (EP) .............................................. 97200765

(51) Int. Cl.$^7$ .......................... C12N 5/10; C12N 15/29; C12N 15/82; C07H 21/04; A01H 1/00
(52) U.S. Cl. .................... 800/290; 800/298; 435/320.1; 435/419; 435/468; 536/23.6
(58) Field of Search .............................. 800/290, 298; 435/468, 419, 320.1; 536/23.6

(56) References Cited

FOREIGN PATENT DOCUMENTS

WO    WO 92/09685    6/1992 ............ C12N/5/00

OTHER PUBLICATIONS

De Veylder et al, "CKS1At overexpression in *Arabidopsis thaliana* inhibits growth by reducing meristem size and inhibiting cell–cycle progression", 2001, The Plant Journal vol. 25 No. 6, pp. 617–626.*
Finley et al, Genbank Accession No. U40077.*
Quin, L.–X., and Bergounioux, C., GenBank Sequence Accession No. L77084, Jun. 15, 1996, revised publication Oct. 24, 2001.
Newman, T., et al., EMBL Accession No. R87032, published Aug. 19, 1995.
Newman, T., et al., EMBL Accession No. T88127, published Apr. 1, 1995.
Finley, R. L., et al., (1994) "Interaction mating reveals binary and ternary connections between Drosophila cell cycle regulators", *Proc. Natl. Acad. Sci.*, 91:12980–12984.
Finley, R. L., et al., EMBL Accession No. U40077, published Jan. 2, 1996.
Birck, C., et al., (1995) "Oligomerization state in solution of the cell cycle regulators p13$^{suc1}$ from the fission yeast and p9$^{cksphy}$ from the myxomycete Physarum, two members of the cks family", *FEBS Letters*, 363:145–150.
Harini, I., et al., Abstract No. 85003, *Biological Abstracts*, vol. 91.
Nagl, W., (1993) "Induction of High Polyploidy in Phaseolus Cell Cultures by the Protein Kinase Inhibitor K–252A", *Plant Cell Rep*, 12(3):170–174.
De Veylder, L., et al., (1997) "The Arabidopsis Cks1At protein binds the cyclin–dependent kinases Cdc2aAt and Cdc2bAt" *FEBS Letters*, 412:446–452.
Doerner, P., et al., (1996) "Control of root growth and development by cyclin expression" *Nature* 380:520–523.
Doonan, J., (1996) "Plant growth: roots in the cell cycle" *Current Biology*, 6(7):788–789.
Hemerly, A., et al. (1995) "Dominant negative mutants of the Cdc2 kinase uncouple cell division from iterative plant development" *Embo Journal*, 14(16):3925–3936.
Bell, M. H., et al. (1993) "Tobacco plants transformed with cdc25, a mitotic inducer from fission eyast" *Plant Molecular Biology*, 23:445–451.
John, P.C.L., et al., Abstract No. 16351, *Biological Abstracts, BA92*.
Grafi, G., e al. (1995) "Endoreduplication in maize endosperm: Involment of M phase–promoting factor inhibition and induction of S phase–related kinases" *Science*, 269:1262–1264.
Grafi, G., et al. (1996) "A maize cdna encoding a member of the retinoblastoma protein family: involvement in endoreduplication" Proceedings of the National Academy of Sciences of USA, 93(17):8962–8967.
Nagl, W., et al. (1995) "cdc2–kinases, cyclins, and the switch from proliferation to polyploidization" *Protoplasma*, 188:143–150.

* cited by examiner

Primary Examiner—Elizabeth F. McElwain
Assistant Examiner—Cynthia Collins
(74) Attorney, Agent, or Firm—Ann R. Pokalsky; Dilworth & Barrese, LLP

(57) ABSTRACT

The present invention provides a new Arabidopsis thaliana nucleotide sequence and polypeptide sequence having a molecular weight of about 10.5 kDa. Modulation of the expression of the polypeptides encoded by the nucleotide sequences according to the invention has an advantageous influence on plant cell division characteristics especially on the endoreduplication whereby plant cell size and storage capacity of plant cells is influenced.

22 Claims, No Drawings

METHOD AND MEANS FOR MODULATING PLANT CELL CYCLE PROTEINS AND THEIR USE IN PLANT CELL GROWTH CONTROL

The present invention relates to a novel cell cycle gene in plants and to a method for controlling or altering growth characteristics of a plant and/or a plant cell comprising introduction and/or expression of one or more cell cycle regulatory protein functional in a plant or parts thereof and/or one or more nucleic acid sequence encoding such proteins. Optionally, said sequences are placed under the control of a foreign control sequence in said plant and/or plant cell.

Also provided in the present invention is a method for modulating endoreduplication in plants, plant cells or parts thereof, by genetic engineering techniques. In a preferred embodiment endoreduplication in plants, plant cells or parts thereof is modulated by modifying the plant cell cycle.

Cell division is fundamental for growth in humans, animals and plants. Prior to dividing in two daughter cells, the mother cell needs to replicate its DNA. The cell cycle is traditionally divided into 4 distinct phases:

G1: the gap between mitosis and the onset of DNA synthesis;
S: the phase of DNA synthesis;
G2: the gap between S and mitosis.
M: mitosis, the process of nuclear division leading up to the actual cell division.

The distinction of these 4 phases provides a convenient way of dividing the interval between successive divisions. Although they have served a useful purpose, a recent flurry of experimental results, much of it as a consequence of cancer research, has resulted in a more intricate picture of the cell cycle's "four seasons" (K. Nasmyth, Science 274, 1643–1645, 1996; P. Nurse, Nature, 344, 503–508, 1990)

The underlying mechanism controlling the cell cycle control system has only recently been studied in greater detail. In all eukaryotic systems, including plants, this control mechanism is based on two key families of proteins which regulate the essential process of cell division, namely protein kinases (cyclin dependent kinases or CDKs) and their activating associated subunits, called cyclins. The activity of these protein complexes is switched on and off at specific points of the cell cycle. Particular CDK-cyclin complexes activated at the G1/S transition trigger the start of DNA replication. Different CDK-cyclin complexes are activated at the G2/M transition and induce mitosis leading to cell division.

Each of the CDK-cyclin complexes execute their regulatory role via modulating different sets of multiple target proteins. Furthermore, the large variety of developmental and environmental signals affecting cell division all converge on the regulation of CDK activity. CDKs can therefore be seen as the central engine driving cell division.

In animal systems and in yeast, knowledge about cell cycle regulations is now quite advanced. The activity of CDK-cyclin complexes is regulated at five levels: (i) transcription of the CDK and cyclin genes; (ii) association of specific CDK's with their specific cyclin partner; (iii) phosphorylation/dephosphorylation of the CDK and cyclins; (iv) interaction with other regulatory proteins such as SUC1/CKS1 homologues and cell cycle kinase inhibitors (CKI); and (v) cell cycle phase-dependent destruction of the cyclins and CKIs.

The study of cell cycle regulation in plants has lagged behind that in animals and yeast. Some basic mechanisms of cell cycle control appear to be conserved among eukaryotes, including plants. Plants were shown to also possess CDK's, cyclins and CKI's. However plants have unique developmental features which are reflected in specific characteristics of the cell cycle control. These include for instance the absence of cell migration, the formation of organs throughout the entire lifespan from specialized regions called meristems, the formation of a cell wall and the capacity of non-dividing cells to re-enter the cell cycle. Another specific feature is that many plant cells, in particular those involved in storage (e.g. endosperm), are polyploid due to rounds of DNA synthesis without mitosis. This so-called endoreduplication is intimately related with cell cycle control.

Due to these fundamental differences, multiple components of the cell cycle of plants are unique compared to their yeast and animal counterparts. For example, plants contain a unique class of CDKs, such as CDC2b in Arabidopsis, which are both structurally and functionally different from animal and yeast CDKs.

The further elucidation of cell cycle regulation in plants and its differences and similarities with other eukaryotic systems is a major research challenge. Strictly for the case of comparison, some key elements about yeast and animal systems are described below in more detail.

As already mentioned above, the control of cell cycle progression in eukaryotes is mainly exerted at two transition points: one in late $G_1$, before DNA synthesis, and one at the $G_2/M$ boundary. Progression through these control points is mediated by cyclin-dependent protein kinase (CDK) complexes, which contain, in more detail, a catalytic subunit of approximately 34-kDa encoded by the CDK genes. Both *Saccharomyces cerevisiae* and *Schizosaccharomyces pombe* only utilise one CDK gene for the regulation of their cell cycle. The kinase activity of their gene products $p34^{CDC2}$ and $p34^{CDC28}$ in *Sch. pombe* and in *S. cerevisiae*, respectively, is dependent on regulatory proteins, called cyclins. Progression through the different cell cycle phases is achieved by the sequential association of $p34_{CDC2/CDC28}$ with different cyclins. Although in higher eukaryotes this regulation mechanism is conserved, the situation is more complex since they have evolved to use multiple CDKs to regulate the different stages of the cell cycle. In mammals, seven CDKs have been described, defined as CDK1 to CDK7, each binding a specific subset of cyclins.

In animal systems, CDK activity is not only regulated by its association with cyclins but also involves both stimulatory and inhibitory phosphorylations. Kinase activity is positively regulated by phosphorylation of a Thr residue located between amino acids 160–170 (depending on the CDK protein). This phosphorylation is mediated by the CDK-activating kinase (CAK) which interestingly is a CDK/cyclin complex itself. Inhibitory phosphorylations occur at the ATP-binding site (the Tyr15 residue together with Thr14 in higher eukaryotes) and are carried out by at least two protein kinases. A specific phosphatase, CDC25, dephosphorylates these residues at the $G_2/M$ checkpoint, thus activating CDK activity and resulting in the onset of mitosis.

CDK activity is furthermore negatively regulated by a family of mainly low-molecular weight proteins, called cyclin-dependent kinase inhibitors (CKIs). Kinase activity is inhibited by the tight association of these CKIs with the CDK/cyclin complexes.

The SUC1/CKS1 proteins represent another class of components of CDK complexes. The SUC1 and CKS1 genes were originally identified in *Sch. pombe* and *S.cerevisiae*, respectively as suppressors of certain temperature-sensitive CDC2/CDC28 alleles. Mutant p34$^{CDC2}$ proteins suppressible by SUC1 overexpression were shown to have a reduced affinity for the SUC1 protein. Homologues of SUC1/CKS1 have since then been identified in a wide range of organisms, including human, Drosophila and Xenopus. The conserved interaction between SUC1/CKS1 proteins with CDKs allows purification of homologous CDKs from other species using affinity chromatography.

More than one decade after their initial discovery, the function of the SUC1/CKS1 genes is still not resolved. In yeasts, both SUC1 and CKS1 are essential genes, as was demonstrated by gene disruption. Cells deleted for SUC1 show mitotic spindles of varying lengths and condensed chromosomes, typical for a late mitotic arrest. The presence of high cyclin levels suggests that this arrest is attributed to the inability to destroy the mitotic cyclins, which is a prerequisite to leave M phase. Mitotic cyclins are normally destroyed by the ubiquitin-dependent proteosomal pathway. An essential component in this destruction pathway is a multiprotein complex called the anaphase-promoting complex (APC) or cyclosome. Mutations in the APC result in a stabilisation of mitotic cyclins and cause an anaphase arrest.

However, in addition, the presence of high concentrations of SUC1/CKS1 blocks cell cycle progression. Analysis of Xenopus cell-free extracts indicates that the high SUC1/CKS1 levels inhibit the onset of mitosis by interfering with the dephosphorylation of the CDK Tyr15 residue by CDC25.

Taken together, the appearance of multiple phenotypes suggests different roles for the SUC1/CKS1 protein. Amongst these, it may function as a docking factor for both positive and negative regulators of CDK complexes. This model is supported by a recent crystallographic study of a human SUC1/CKS1 homologue, CKSHs1, complexed with CDK2. As a monomer SUC1/CKS1 proteins have a large hydrophobic surface and a cluster of positively charged residues, which represents a putative phosphate anion-binding site. Binding of CKSHs1 to CDK2 involves the hydrophobic surface and positions the anion-binding site close to the substrate recognition site of CDK2, suggesting that CKSHs1 may act in the targeting of CDK2 to already phosphorylated substrates. Both CDC25 and APC are positively regulated by CDK phosphorylation. The observed phenotypes concerning SUC1/CKS1 overexpression and deletion may therefore be a consequence of the inability of the CDK complexes to recognise CDC25 and components of the APC as substrates, with cell cycle arrest as a result.

With respect to cell cycle regulation in plants a summary of the state of the art is given below. In Arabidopsis, thusfar only two CDK genes have been isolated, CDC2aAt and CDC2bAt, of which the gene products share 56% amino acid identity. Both CDKs are distinguished by several features. First, only CDC2aAt is able to complement yeast p34$^{CDC2/CDC28}$ mutants. Second, CDC2aAt and CDC2bAt bear different cyclin-binding motifs (PSTAIRE and PPTALRE, respectively), suggesting they may bind distinct types of cyclins. Third, although both CDC2aAt and CDC2bAt show the same spatial expression pattern, they exhibit a different cell cycle phase-specific regulation. The CDC2aAt gene is expressed constitutively throughout the whole cell cycle. In contrast, CDC2bAt mRNA levels oscillate, being most abundant during the S and $G_2$ phases.

In addition, multiple cyclins have been isolated from Arabidopsis. The majority displays the strongest sequence similarity with the animal A- or B-type class of cyclins, but also D-type cyclins have been identified. Although the classification of Arabidopsis cyclins is mainly based upon sequence similarity, limited data suggests that this organisation corresponds with differential functions of each cyclin class. Direct binding of any cyclin with an Arabidopsis CDK subunit has, however, not yet been demonstrated.

In order to manage problems related to plant growth, plant architecture and/or plant diseases, it is believed to be of utmost importance to identify and isolate plant genes and gene products involved in the regulation of the plant cell division, and more particularly coding for and interacting with CDK's and/or their interacting proteins, responsible for the control of the cell cycle and the completion of the S and M phase of the cell cycle. If such novel genes and/or proteins have been isolated and analysed, the growth of the plant as a whole can be influenced. Also, the growth of specific tissues or organs and thus the architecture of the plant can be modified.

In the present invention a two-hybrid screen was exploited to isolate new gene products interacting with CDC2aAt. A positive clone indicative of a hitherto unknown plant cell cycle regulatory nucleotide sequence was identified. A homology search in databases showed the identification of a very first plant homologue of the SUC1 gene from Sch. pombe and the CKS1 gene from S. cerevisiae. Surprisingly the novel plant CKS1 homologue (having less than 50% homology at amino acid level with the corresponding yeast genes) was able to rescue a Sch. pombe temperature-sensitive CDC2 mutant. This confirmed that the newly isolated plant sequence could, also from a functional viewpoint, be designated as a CKS1 homologue. The Arabidopsis gene was designated CKS1At, for CDK-associating subunit from Arabidopsis thaliana.

Thus a novel plant nucleotide sequence and polypeptide sequence, having a molecular weight of about 10.5 kDa, are provided.

The DNA sequence of CKS1At comprises the nucleotide sequence defined in SEQ.ID NO.1 encoding for a protein as defined in SEQ.ID.NO.3 or for a protein having substantially the same amino acid sequence as the protein defined in SEQ.ID.NO.3.

The coding nucleotide sequence for CKS1At in SEQ.ID.NO. 1 starts at the first ATG codon (position 1) and terminates at codon AAG (position 261).

Using a nucleic acid amplification technology, such as the polymerase chain reaction (PCR), a genomic DNA fragment containing introns was isolated comprising the sequence defined in SEQ.ID.NO. 2.

Thus the invention provides an isolated and/or recombinant nucleic acid molecule, preferably DNA, encoding at least a functional part of a plant CKS1 protein, which protein in Arabidopsis thaliana comprises the sequence as depicted in SEQ.ID.NO.3 or SEQ.ID.NO.4 or a functional part thereof.

A further part of the invention is a nucleic acid molecule comprising at least a part of the sequence as depicted in SEQ.ID.NO.1 or SEQ.ID.NO.2 or a sequence substantially homologous thereto. In a preferred embodiment, this nucleic acid molecule is isolated from a monocotyledonous or dicotyledonous plant species.

A further embodiment of the current invention is a nucleic acid molecule comprising at least a part of the sequence as depicted in SEQ.ID.NO.1 or SEQ.ID.NO.2 or a sequence which hybridizes under conventional, preferably under stringent, conditions to at least a part of said sequence or its complementary sequence.

Alternatively, the nucleotide sequence depicted in SEQ.ID.NO.1 or SEQ.ID.NO.2 can be used to design so-called amplification primers for use in a nucleic acid amplification technique. Said primers can be used in a particular amplification technique to identify and isolate substantially homologous nucleic acid molecules from other plant species. The design and use of said primers is known by a person skilled in the art. Preferably such amplification primers comprise a contiguous sequence of at least 6 nucleotides, in particular 13 nucleotides or more, identical or complementary to the nucleotide sequence depicted in SEQ.ID.NO.1 or SEQ.ID.NO.2.

In addition, the nucleic acid molecule provided in SEQ.ID.NO.1 or SEQ.ID.NO.2 or parts of these sequences can be used to select substantially homologous sequences present in other plants than *Arabidopsis thaliana*. It has been shown according to the invention that for instance riboprobes from CKS1At hybridize with CKS1 RNA from different plant species.

The *Arabidopsis thaliana* polypeptide according to the invention comprises the amino acid sequence as defined in SEQ.ID.NO.3.

CKS1At protein binds, in vitro and in vivo, to CDKs such as CDC2aAt and CDC2bAt. The CKS1At protein can also be used to complement *Sch.pombe* SUC1 disruptants. Furthermore the CKS1At protein can be used to rescue a *Sch.pombe* temperature-sensitive CDC2 mutant.

Therefore a further part of the invention are polypeptides, preferably plant polypeptides which have, compared to the CKS1At protein, comparable or identical characteristics in terms of binding to cyclin dependent kinases, in particular plant cyclin dependent kinases.

To the scope of the current invention also belong plant polypeptides which have, compared to the CKS1At protein, similar properties to complement *Sch.pombe* SUC1 disruptants and/or to rescue *Sch.pombe* temperature-sensitive CDC2 mutants such as the CDC2-L7 strain.

Fragments of the above mentioned polypeptide, such as the first 72 amino acids as illustrated in SEQ.ID.NO. 4, also belong to the invention. The last 15 amino acids of CKS1At, including the polyglutamine stretch, are dispensable for the binding of both CDC2aAt and CDC2bAt. It is likely that these amino acids are involved in interactions with other proteins.

The CKS1At mutant E61Q (which means a mutant protein where at position 61 of the wild type CKS1At, the Glu residue is replaced by the Gln residue) has reduced binding affinity for CDKs. Overexpression of the CKS1At protein caused a G2-specific cell cycle arrest in fission yeast. In contrast, the E61Q mutated protein does not arrest cell cycle progression. This demonstrates that the E61-residue is an important amino acid in CKS1At for interaction with CDKs. A second point mutation (P62G, replacement of proline at position 62 by glycine) in CKS1At also showed reduced binding activity for CDK. The use of this inactive mutants to modulate the cell cycle in plant cells, plant tissues, plant organs or whole plants is part of this invention.

Increased expression levels in maturing leaves indicate a role for CKS1At in endoreduplication, whereas the lack of CDC2aAt and CDC2bAt expression in these tissues suggest the presence of an as yet unidentified CDK protein in Arabidopsis, specifically involved in endoreduplication. These results suggest that CKS1At can also interact with a novel, as yet unidentified CDK protein in Arabidopsis.

Part of the invention is also a polypeptide comprising at least a functional part of a plant CKS1 protein encoded by a nucleic acid sequence comprised in a nucleic acid molecule according to the invention. An example for this is that the polypeptide or a fragment thereof according to the invention is embedded in another amino acid sequence.

To the scope of the present invention also belong numerous variations on the disclosed sequences which could be prepared by those skilled in the art using known techniques. The polypeptides encoded by the nucleic acid sequences above mentioned may be modified by varying their amino acid sequence without substantially altering their function. Derivatives of the polypeptides disclosed herein, such as polypeptides carrying single or multiple amino acid substitutions, deletion and/or additions, are included within the present invention.

A further part of the invention is a polypeptide comprising at least a part of the sequence as provided in SEQ.ID.NO3 or SEQ.ID.NO4 or a polypeptide with at least 40%, and preferably more than 69% homology at amino acid level, such sequence preferably being a plant polypeptide.

Plant cell division can conceptually be influenced in three ways (i) inhibiting or arresting cell division, (ii) maintaining, facilitating or stimulating cell division or (iii) uncoupling DNA synthesis from mitosis and cytokinesis. Being able to uncouple S phase from M phase would create opportunities to inhibit or stimulate the level of endoreduplication in specific cells, tissues and/or organs from living organisms, and more in particular in plant cells, plant tissues, plant organs or whole plants.

To analyse the industrial applicabilities of CKS1At and any plant homologue, for the first time transformed plants overproducing CKS1At were created. Surprisingly, the transformed plants do show modulated endoreduplication. To further analyse whether other plant cell cycle genes could also modulate endoreduplication in plants, transformed plants overproducing a plant cyclin dependent kinase were created, and more in particular plants overexpressing a plant specific dependent kinase such as CDC2b from *Arabidopsis thaliana* were created. Surprisingly, modulated (and more particular enhanced) endoreduplication could clearly be demonstrated in these transformed plants. In yet an alternative set of experiments, transformed plants expressing a dominant negative mutant of a cyclin dependent kinase were created. More in particular, plants were created which express a mutant cyclin dependent kinase still able to bind to other regulatory cell cycle proteins but with no or limited activity. Even more surprisingly, also these transformed plants demonstrated a significantly modulated level of endoreduplication in comparison with control plants.

Therefore part of this invention is the use of plant cell cycle genes and/or plant cell cycle proteins to modulate endoreduplication in plant cells, plant tissues, plant organs and/or whole plants. The man skilled in the art can use cell cycle genes and proteins from other organisms such as yeast and animals to modulate endoreduplication in plant cells, plant tissues, plant organs and/or whole plants since the functionality of plant cell cycle genes and proteins to modulate endoreduplication is herewith disclosed. The use of these genes and proteins to modulate endoreduplication is therefore also an embodiment of this invention.

In a further preferred embodiment endoreduplication in plant cells, plant tissues, plant organs or whole plants is modulated via enhancing or reducing the expression and/or the activity of a CKS1 gene or CKS1 gene product, preferably a plant CKS1 gene or plant CKS1 gene product. In a further preferred embodiment overexpression of CKS1At is used to enhance endoreduplication in plant cells, plant tissues, plant organs or whole plants.

In yet another preferred embodiment, cyclin dependent kinases, preferably plant cyclin dependent kinase and more preferably plant specific cyclin dependent kinase such as CDC2b from *Arabidopsis thaliana*, are used to modulate endoreduplication in plant cells, plant tissues, plant organs and/or whole plants. In a further preferred embodiment overexpression of a CDC2b from Arabidopsis is used to enhance endoreduplication in plant cells, plant tissues, plant organs or whole plant.

In a further preferred embodiment expression of a dominant negative mutant of cyclin dependent kinases, such as mutant cyclin dependent kinases which still have binding activities for regulatory cell cycle proteins but have no or only limited kinase activity, is used to modulate endoreduplication in plant cells, plant tissues, plant organs and/or whole plants. One example of such dominant negative mutant is an *Arabidopsis thaliana* CDC2b variant wherein the aspartic acid at position 161 is replaced by asparagine.

In a further preferred embodiment, expression of the dominant negative mutant of a plant CDC2b is used to modulate the endoreduplication in plant cells, plant tissue, plant organs or whole plants.

Because the present invention for the first time clearly demonstrates that it is possible to modulate endoreduplication in plants or parts thereof by modulating the expression and/or activity of a gene or protein through genetic engineering, the scope of the invention also contemplates a general method for modulating endoreduplication by modifying the expression and/or activity of specific genes or gene products through genetic engineering. A preferred embodiment provides the use of genetic engineering to modulate endoreduplication in plant cells, plant tissue, plant organs and/or whole plants.

With reference to the above, an important aspect of the current invention is a method for modulating endoreduplication in monocotyledonous or dicotyledonous plants or parts thereof by modifying the plant cell division. In a preferred embodiment one or more cell cycle genes or plant cell cycle genes, preferably operably linked to control sequences, are for instance used to specifically modulate endoreduplication in transformed plants, particularly:

in the complete plant in selected plant organs, tissues or cell types under specific environmental conditions, including abiotic stress such as cold, heat, drought or salt stress or biotic stress such as pathogen attack during specific developmental stages.

In a further preferred embodiment, one or more cell cycle genes or plant cell cycle genes, preferably operably linked to a control sequence are used to modulate endoreduplication in storage cells, storage tissues and/or storage organs of plants or parts thereof. Preferred target storage organs and parts thereof for the modulation of endoreduplication according to the invention, are for instance seeds (such as from cereals, oilseed crops), roots (such as in sugar beet), tubers (such as in potato) and fruits (such as in vegetables and fruit species). Furthermore it is expected that increased endoreduplication in storage organs and parts thereof correlates with enhanced storage capacity and as such with improved yield.

In yet another embodiment of the invention, a plant with modulated endoreduplication in the whole plant or parts thereof can be obtained from a single plant cell by transforming the cell, in a manner known to the skilled person, with a cell cycle gene, preferably a plant cell cycle gene and, not necessarily but preferably operably linked to a control sequence. In a preferred embodiment such transformation is performed with a CKS1 gene, a CDC2 gene and/or a dominant negative mutant of a CDC2 gene.

In a further preferred embodiment such transformed plants can be obtained by transforming with a plant CKS1 gene, a plant CDC2 gene and/or a dominant negative mutant of a plant CDC2 gene.

In a further preferred embodiment such transformation is performed with a nucleic acid molecule according to claim 1 and/or the Arabidopsis CDC2b gene and/or a dominant negative mutant of the Arabidopsis CDC2b gene.

Any obtained transformed plant with modulated endoreduplication can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention.

The current invention also demonstrates that CKS1, preferably a plant CKS1 and more preferably CKS1At, can be used to interfere with the plant cell cycle and can be used more specifically to prevent entering mitosis and thus inhibit or even arrest cell division in plants or parts thereof. In a particular preferred embodiment of this invention, cell division is inhibited or arrested in plant meristems.

Alternatively, expression studies (see examples) strongly indicate that in plants or parts thereof, low levels of expression and/or activity of CKS1 are correlated with non-dividing cells. The present invention therefor further embraces a method to use CKS1 preferably a plant CKS1 and more preferably CKS1At, to maintain, facilitate or stimulate cell division in plants or parts thereof. In a particular preferred embodiment, cell division is maintained, facilitated or enhanced in plant meristems. In another preferred embodiment cell division is induced in resting cells.

A further part of this invention is a method for transforming plants with CKS1, preferably plant CKS1 according to the present invention, not necessarily but preferably operably linked to a control sequence. Using this approach, and since cell division is a crucial element in determining the growth and shape of a plant or parts thereof, it is expected that defined modulation of the expression and/or activity of plant CKS1 will allow the production of transformed plants, with modulated growth.

Methods to modify the expression levels and/or the activity of CKS1 preferably plant CKS1, are known to persons skilled in the art and include for instance overexpression, co-suppression, the use of ribozymes, anti-sense strategies, gene silencing approaches.

The invention is in principle applicable to any plant and crop that can be transformed with any of the transformation method known to those skilled in the art and includes for instance corn, wheat, barley, rice, oilseed crops, cotton, tree species, sugar beet, cassava, tomato, potato, numerous other vegetables, fruits.

Similarly, the invention can also be used to modulate the cell division and the growth of cells, preferentially plant cells, in in vitro cultures.

Further in accordance with the invention chimeric genes are provided, comprising the following operably linked polynucleotides:

a. a nucleic acid molecule according to claim 1 to 3 b. one or more control sequences

Alternatively, said chimeric genes comprise the following operably linked polynucleotides:

a. a dominant negative plant CDC2 mutant with characteristics such as the D161N mutant of Arabidopsis CDC2b b. one or more control sequences Vectors or expression vectors comprising a nucleic acid molecule according to claim 1 or comprising chimeric genes such as described above are also considered as part of the invention.

Part of the invention is also a plant cell carrying at least a functional part of the nucleic acid molecule according to the invention or a chimeric gene as described above.

The present invention is also directed to a transgenic plant carrying a plant cell comprising a nucleic acid molecule according to claim 1 or a chimeric gene as described above.

A transgenic plant is obtained through a process of regenerating said plant starting from a plant cell having as part of its genetic material the nucleic acid molecule according to the invention or a chimeric gene as described above. Progeny of the plant and/or plant material such as flowers, fruit, leaves, pollen, seeds, seedlings or tubes obtainable from said transgenic plant also belong to the current invention.

Also part of the invention are antibodies recognising a plant CKS1 protein or a part thereof. Another part of the invention is the use of antibodies raised against CKS1At to identify and isolate other plant CKS1 proteins and genes.

In order to clarify what is meant in this description by some terms a further explanation is hereunder given.

The polypeptides of the present invention are not necessarily translated from a designated nucleic acid sequence; the polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art.

The terms "gene(s)", "polynucleotide", "nucleic acid sequence", "nucleotide sequence", "DNA sequence" or "nucleic acid molecule(s)" as used herein refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occuring nucleotides with an analog.

"Recombinant nucleic acid molecule" as used herein refers to a polynucleotide of genomic, cDNA, semisynthetic or synthetic origin which, by virtue of its origin or manipulation (1) is linked to a polynucleotide other than that to which it is linked in nature or, (2) does not occur in nature.

An "expression vector" is a construct that can be used to transform a selected host cell and provides for expression of a coding sequence in the selected host. Expression vectors can for instance be cloning vectors, binary vectors or integrating vectors.

A "coding sequence" is a nucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

"Control sequence" refers to regulatory DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

The terms "protein" and "polypeptide" used in this application are interchangeable. "Polypeptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

"Fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids.

The term "antibody" includes, without limitation, chimeric antibodies, altered antibodies, univalent antibodies, bi-specific antibodies, Fab proteins or single-domain antibodies. In many cases, the binding phenomena of antibodies to antigens is equivalent to other ligand/anti-ligand binding. The antibody can be a monoclonal or a polyclonal antibody.

"Transformation" as used herein, refers to the transfer of an exogenous polynucleotide into a host cell, irrespective of the method used for the transfer. The polynucleotide may be transiently or stably introduced into the host cell and may be maintained non-integrated, for example, as a plasmid, or alternatively, may be integrated into the host genome. Many types of vectors can be used to transform a plant cell and many methods to transform plants are available. Examples are direct gene transfer, pollen-mediated transformation, plant RNA virus-mediated transformation, Agrobacterium-mediated transformation, liposome-mediated transformation, transformation using wounded or enzyme-degraded immature embryos, or wounded or enzyme-degraded embryogenic callus. All these methods and several more are known to persons skilled in the art. The resulting transformed plant cell can then be used to regenerate a transformed plant in a manner known by a skilled person.

"Functional part of" means that said part to which subject it relates has substantially the same activity as the subject itself, although the form, length or structure may vary.

The term "substantially homologous" refers to a subject, for instance a nucleic acid, which is at least 50% identical in sequence to the reference when the entire ORF (open reading frame) is compared, where the sequence identity is preferably at least 70%, more preferably at least 80%, still more preferably at least 85%, especially more than about 90%, most preferably 95% or greater, particularly 98% or greater. Thus, for example, a new nucleic acid isolate which is 80% identical to the reference is considered to be substantially homologous to the reference. Sequences that are substantially homologous can be identified by comparing the sequences using standard software available in sequence data banks, or in a Southern hybridisation experiment under, for instance, conventional or preferably stringent conditions as defined for that particular system.

Similarly, in a particular embodiment, two amino acid sequences, when proper aligned in a manner known to a skilled person, are "substantially homologous" when more than 40% of the amino acids are identical or similar, or when more preferably more than about 60% and most preferably more than 69% of the amino acids are identical or similar (functionally identical).

"Sense strand" refers to the strand of a double-stranded DNA molecule that is homologous to a mRNA transcript thereof. The "anti-sense strand" contains an inverted sequence which is complementary to that of the "sense strand".

"Cell cycle" or "cell division" means the cyclic biochemical and structural events associated with growth and with division of cells, and in particular with the regulation of the replication of DNA and mitosis. The cycle is divided into periods called: $G_0$, $Gap_1$ ($G_1$), DNA synthesis (S), $Gap_2$ ($G_2$), and mitosis (M).

"Cell cycle genes" are genes encoding proteins involved in the regulation of the cell cycle or fragments thereof.

"Plant cell cycle genes" are cell cycle genes originally present or isolated from a plant or fragments thereof.

"Plant cell" comprises any cell derived from any plant and existing in culture as a single cell, a group of cells or a callus. A plant cell may also be any cell in a developing or mature plant in culture or growing in nature.

"Plants" comprises all plants, including monocotyledonous and dicotyledonous plants.

"Plant sequence" is a sequence naturally occurring in a plant.

"Plant polypeptide" is a polypeptide naturally occurring in a plant.

"Cyclin-dependent protein kinase complex" means the complex formed when preferably functional, cyclin associates with a, preferably, functional cyclin dependent kinase. Such complexes may be active in phosphorylating proteins and may or may not contain additional protein species.

"Cell-cycle kinase inhibitor" (CKI) is a protein which inhibit CDK/cyclin activity and is produced and/or activated when further cell division has to be temporarily or continuously prevented.

"Expression" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications.

"Modulation of expression or activity" means control or regulation, positively or negatively, of the expression or activity of a particular protein or nucleotide sequence by methods known to a skilled person.

"Endoreduplication" means recurrent DNA replication without consequent mitosis and cytokinesis.

"Foreign" with regard to a DNA sequence means that such a DNA is not in the same genomic environment in a cell, transformed with such a DNA in accordance with this invention, as is such DNA when it is naturally found in a cell of the plant, bacteria, fungus, virus or the like, from which such a DNA originates.

In the description of the current invention reference is made to the following sequences of the Sequence Listing:

SEQ.ID.NO. 1: coding nucleotide sequence (position 1–261) for CKS1At with flanking non-coding sequences.

SEQ.ID.NO. 2: genomic nucleotide sequence with introns

SEQ.ID.NO. 3: amino acid sequence (position 1–87) obtainable from the coding nucleotide sequence represented in SEQ.ID.NO. 1.

SEQ.ID.NO.4: amino acid sequence (position 1–72) obtainable from the coding nucleotide sequence represented in SEQ.ID.NO. 1.

The present invention is further described by reference to the following non-limiting figures and examples.

Unless stated otherwise in the Examples, all recombinant DNA techniques are performed according to protocols as described in Sambrook et al. (1989), Molecular Cloning: A Laboratory Manual. Cold Spring Harbor Laboratory Press, NY or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, jointly published by BIOS Scientific Publications Ltd (UK) and Blackwell Scientific Publications (UK).

EXAMPLE 1

Two hybrid screen using CDC2aAt as bait

To identify CDC2aAt-interacting proteins a two-hybrid system was used based on GAL4 recognition sites to regulate the expression of both his3 and lacZ reporter genes (Fields et al., 1989). The pGBTCDC2A vector, encoding a fusion protein between the C terminus of the GAL4 DNA-binding domain and CDC2aAt, was constructed by cloning the full-length coding region of CDC2aAt into the pGBT9 vector. For the screening a GAL4 activation domain cDNA fusion library was used, constructed with RNA isolated from 3-week-old Arabidopsis vegetative tissues. The pGBTCDC2A plasmid was cotransformed with the library into the yeast HF7c reporter strain. A total of $10^7$ independent cotransformants were screened for their ability to grow on histidine-free medium. A 3-day incubation at 30° C. yielded 300 colonies. These 300 colonies were then tested for their growth on medium without histidine in the presence of 10 mM 3-amino-1,2,4-triazole (3-AT), reducing the number of positives to 235. Next, these colonies were tested for activation of the lacZ gene, and 143 turned out to be both $His^+$ and $LacZ^+$. After DNA preparation and restriction fragment analysis, of all 143 positive clones three different types of genes were identified.

One class of genes, represented by 139 cDNA clones, contained a small open reading frame coding for a protein of 87 amino acids, with a calculated molecular mass of 10.5 kDa. This gene was represented by at least two independent clones, as indicated by the varying length of their 5' and 3' untranslated regions. The longest clone contained a 5' untranslated region of 15 bp and a 3' untranslated region of 208 bp. A BLAST data base search revealed that this clone (called pGADCKS) encoded a SUC1/CKS1 homologue, whereas the gene is of plant origin. The gene was designated CKS1At for CDK-associating subunit from *Arabidopsis thaliana*.

The specificity of the interaction between CDC2aAt and CKS1At was verified by the retransformation of yeast with pGBTCDC2A and pGADCKS. As controls, pGBTCDC2A and reverse pGADCKS were cotransformed with a vector containing only the GAL4 activation domain (pGAD424) and with the pGBT9 plasmid encoding the GAL4 DNA-binding domain only, respectively. Transformants were plated on medium with or without histidine. Only transformants containing both pGBTCDC2A and pGADCKS were able to grow in the absence of histidine.

EXAMPLE 2

Characterisation of the CKS1At gene

An alignment of the amino acid sequence of CKS1At, encoding a protein of about 10.5 kDa, according to the invention with SUC1/CKS1 homologues from yeasts, human, *Drosophila melanogaster, Xenopus laevis,* and *Patella vulgata* shows a highly conserved region of 70 amino acids (from Gly2 to Leu71) of CKS1At with all non-yeast homologues (67–69% amino acid identity).The level of amino acid identity between CKS1At and SUC1 of *Sch.pombe* on the one hand and CKS1 of *S.cerevisiae* on the other hand, is limited to 49.3% and 49.4% respectively. This is due to the presence of a 9 amino acid sequence inserted into the yeast proteins (from Tyr55 to Leu63 in *Sch.pombe* and from Tyr58 to Leu66 in *S.cerevisiae*). These 9 amino acids are not present in the CKS1At protein. In contrast to other non-yeast homologues, the CKS1At protein has a C-terminal extension of 10–14 amino acids rich in glutamine residues, resembling the situation found for CKS1 of *S. cerevisiae*. Polyglutamine segments are found in a broad variety of proteins and are thought to be involved in protein-protein interactions.

The need for this C-terminal domain for the interaction with CDC2At was assayed using the two-hybrid system. A gene encoding a truncated CKS1At protein was created by mutating the Tyr73 codon to a stop codon, thereby deleting the last 15 amino acids. Subsequently, this mutated gene was cloned in frame with the GAL4 activation domain, resulting in the pGADCDSQ plasmid. This vector was introduced into the HF7c yeast reporter strain, together with pGBTCDC2A or the empty pGBT9 vector. Only transformants harbouring both PGADCKSQ and pGBTCDC2A grew in the absence of histidine, demonstrating that the C-terminal part of CKS1 At was not essential for the binding of CDC2aAt in the yeast system. Therefore, this part of the CKS1At protein might be involved in the interaction with other proteins or may improve the stability of the CDK-CKS1At interaction.

To study the genomic organisation of CKS1At, Arabidopsis DNA was digested with four different enzymes. Hybridisation with the CKS1At-coding region at low stringency showed only one band for every digest, indicating the presence of only one CKS1At gene per haploid genome of Arabidopsis.

EXAMPLE 3

Isolation of a genomic clone of CKS1At

A genomic sequence of the CKS1At clone was obtained by PCR using standard conditions (30 cycles of 1 min. 95° C. denaturation; 1 min. 55° C. annealing and 2 min.of 72° C. elongation). As template 25 ng of genomic *A.thaliana* DNA was used. Primers used were 5'-GAGAGCCATGGGTCAGATCC-3' and 5'-CCAATACTCATAGATCTGTTGC-3'. The obtained PCR product was cloned and sequenced (SEQ.ID.NO.2). Comparison with the cDNA sequence (SEQ.ID.NO.1) revealed the presence of 2 introns in the genomic clone.

EXAMPLE 4

CKS1At can rescue a *Sch. pombe* temperature-sensitive CDC2 mutant

Both SUC1 from *Sch. pombe* and CKS1 from *S. cerevisiae* were initially identified as suppressors of temperature-sensitive alleles of CDC2 and CDC28, respectively. To determine the functionality of the CKS1At protein, we tested whether it is able to rescue the temperature-sensitive *Sch. pombe* CDC2-L7 strain. For this purpose, the full-length CKS1At-coding region was cloned in the pREP3, pREP41, and pREP81 vectors (Maundrell, 1990; Basi et al., 1993), resulting in pREP3CKS, pREP41CKS, and pREP81CKS, respectively. These three vectors contained the thiamine-repressible promoter nmt1 and allowed inducible expression of CKS1At to different levels. Strongest induction could be achieved using the pREP3CKS vector, intermediate with pREP41CKS, and lowest with pREP81CKS. All constructs were introduced into wild-type and CDC2-L7 yeast.

Wild-type *Sch. pombe* cells transformed with pREP81CKS grew normally under both inductive (without thiamine) and non-inductive (with thiamine) conditions. In contrast, in the absence of thiamine, cell growth of wild-type *Sch.pombe* was completely or partially inhibited in cells transformed with pREP3CKS and pREP41CKS, respectively. Microscopic analysis revealed the CKS1At-overexpressing cells to have an elongated phenotype. No cell elongations was seen under non-inductive conditions, nor in cells harboring the empty pREP3 or pREP41 vector, demonstrating that the observed phenotype was linked with CKS1At expression.

The CDC2-L7 transformants were grown in the presence and absence of thiamine, both at the permissive (28° C.) and restrictive (35° C.) temperature. At the permissive temperature a behaviour similar to that of the wild-type strain was observed: cell growth was inhibited in the absence of thiamine for cells transformed with pREP41CKS or pREP3CKS, but not for pREP81CKS transformants. At the restrictive temperature only pREP81CKS- and pREP41CKS-transformed cells grew in the absence of thiamine. No growth was observed in the presence of thiamine, showing that the rescue of the CDC2-L7 strain was specifically associated with the low to intermediate expression levels of CKS1At. At the microscopic level, the rescued CDC2-L7 cells showed a cellular morphology intermediate to that of cells grown at the restrictive temperature and at the permissive temperature.

These results demonstrate that CKS1At has the same properties as the *Sch.pombe* SUC1 gene showing that CKS1At is a true functional homologue of the yeast SUC1 protein.

EXAMPLE 5

Complementation of the Schizosaccharomyces pombe SUC1 disruptant

The SUC1 gene of Schizosaccharomyces pombe was initially identified as a suppressor of specific temperature-sensitive alleles of CDC2 (Hayles et al., 1986, Mol.Gen.Genet.202,291–293).The CKS1At gene of *Arabidopsis thaliana* is capable of rescuing such a temperature sensitive yeast CDC2 allele, demonstrating that CKS1At encodes a true functional homologue of the SUC1 protein (see example 3 of this application). More direct prove was obtained by the complementation of a *S. pombe* SUC1 deleted strain. Deletion of the SUC1 gene is lethal. Cells become either elongated indicating a cell cycle arrest, or are impaired in cellular growth.

The full length coding region of CKS1At was cloned under the control of the thiamine-repressible nmt1 promoter, resulting in the pREP81CKS vector. This vector was introduced in a diploid yeast strain in which one genomic copy of the SUC1 gene was replaced by the ura3 marker. As control the same strain was transformed with the empty pREP81 vector. The transformants were induced to sporulate and the obtained spores were subsequently germinated on nmt1 inducible medium (in the absence of thiamine) and in the absence of uracil. PhloxinB, a dye which marks diploid cells as dark colonies, was added to the medium to be able to distinguish haploid from diploid colonies. Spores obtained from the pREP81 CKS transformed cells gave rise to a mixed population of haploid and diploid cells. In contrast, germinating pREP81 spores only formed diploid colonies. Haploid pREP81CKS cells were restreaked on medium with or without thiamine. Only in the absence of thiamine cell growth was observed, demonstrating that the rescue of the SUC1 disruptant is correlated with the expression of the CKS1At gene and that CKS1At can functionally replace SUC1.

EXAMPLE 6

Expression analysis of CKS1At

The CKS1At expression levels in different Arabidopsis tissues were studied by RNA blot hybridization analysis. Total RNA was extracted from rosette leaves, roots, stems, flowers, siliques, and actively dividing cell suspensions. Using a CKS1At antisense riboprobe a hybridizing band of approximately 600 bp was detected in all tissues, excluding siliques. CKS1At transcripts were most abundant in stems and cell suspensions and only slightly lower in flowers and roots.

To analyze CKS1At expression at the cellular level, in situ hybridizations were performed using both antisense and sense riboprobes. For gene expression analysis in roots we used radish, which is closely related to Arabidopsis, but which offers the advantage of an increased root diameter and cell number in each tissue, facilitating interpretation of the results. Strong CKS1At expression was seen in the meristematic and elongation zone of the main root. Expression decreased in the differentiating zone, but was still detectable in the vascular tissue. No detectable expression was seen in the root cap and the quiescent centre, which have low mitotic activity. During lateral root formation CKS1At expression was strongly induced in the meristem and adjacent vascular system.

Whole-mount in situ hybridizations performed on 7-day-old Arabidopsis seedlings confirmed the expression pattern seen in the radish roots. Whole-mount hybridizations also revealed strong expression in the shoot apical meristem and in leaf primordia. During flower development a strong hybridization signal was observed in flower buds, but its intensity decreased in maturing flowers. In all tissues analyzed, no signal was observed using the sense control probe.

In situ hybridizations performed on sections of shoot meristems of 2-month-old Arabidopsis plants exhibited strong CKS1At expression in the tunica and periphery of the apical dome. A lower hybridization signal was observed in the central zone of the meristem. The observed signal was not uniformly distributed, but rather showed some patchiness. Signals were often associated with vascular tissue. Interestingly, an increase of the CKS1At hybridization signal was noticed as leaves matured. No signals were observed using a sense probe as a control. All these characteristics point to a correlation between CKS1At expression and cell division.

A strong CKS1At hybridisation signal was also observed in maturing leaves. Mitotic index determination showed that these cells stop to divide. However, visualization of the pattern of DNA replication by $[^3H]$-thymidine incorporation demonstrated that in these tissues endoreduplication occured. The matching of the pattern of CKS1At expression with that of endoreduplication in the maturing leaves demonstrates that the CKS1At protein is involved in the process of endoreduplication. The lack of CDC2aAt and CDC2bAt expression in maturing leaves points to the possible presence of a third, yet unidentified, class of CDK proteins in Arabidopsis. The CKS1At apparently interacts with this novel class of CDK proteins.

EXAMPLE 7

Production of CKS1At in plants

Following the polymerase chain reaction technology (PCR) the CKS1At coding region was amplified using the primers 5'GAGAGCCATGGGTCAGATCC3' and 5'CCAATACTCATAGATCTGTTGC3'. The PCR fragment was cut with NcoI and Bgl II and cloned into the NcoI and BamHI restriction sites of the vector pH35S (Hemerly et al., 1995, The EMBO Journal Vol.14,p.3925–3936). The cassette 35S-CKS1At-3' NOS was cloned in the binary vector pGSV4 (Herouart et al., 1994, Plant Physiol.104, p.873–880) and transfered to Agrobacterium tumefaciens. The constructs were introduced in Niciotiana tabacum cv. petit havana (SR1) plants by the leaf disk protocol (Horsch et al., 1985,Science 227, p.1229–1231) and in *Arabidopsis thaliana* using the root transformation protocol.

Primary transformants were selfed and characterized by Northern and Western blotting using 3 week old plantlets. Expression levels were compared with those of a non-transformed plant. In the control plants low levels of mRNA and protein were only visible upon long exposure times since expression of CKS1At is mainly restricted to the mitotic and endoreduplicating cells of the meristems. Among the *Arabidopsis thaliana* CKS1At transformed plants, 5 lines showed moderate CKS1At mRNA expression levels and 1 line showed high mRNA levels. Western blotting using a CKS1At specific antibody showed that the detected amount of CKS1At protein correlates with the observed mRNA levels. For tobacco, CKS1At transformed plants were also regenerated. Two plants showed strong CKS1At mRNA expression while 7 plants showed a moderate expression level. Western blotting using a CKS1At specific antibody showed that the detected amount of CKS1At protein also correlates with the observed mRNA levels.

EXAMPLE 8

Anatomical analyses of root and shoot meristems of CKS1At-overproducing transgenic Arabidopsis plants.

Several independent CKS1At-overproducing lines were grown on vertical plates on standard growth medium (Valvekens et al.,1988, Proc. Natl. Acad. Sci. 85: 5536–5540) in a 16-hr-light/8-hr-dark cycle at 23° C. and 60% room humidity. Root elongation was measured and compared with wild-type (C24) plants. No strieking differences in root growth could be determined and the overall morphology of the transgenic plants looked completely normal. Subsequently, a detailed microscopically analysis was performed on wild-type and transgenic plants in order to detect anatomical deviations from wild-type shoot and root meristem structure. Therefore shoot and root meristems were embedded in a plastic resin (Technovit 7100, Heraeaus Kulzer, Wehrheim, Germany) in such a way that perfectly longitudinally oriented sections could be performed (Scheres et al., 1994, Development 120: 2475–2487).

The sections were stained using different procedures to visualise cells, nuclei, nucleoli and chromosomes: 0.05% toluidine blue-O (Merck), Haematoxyline Heidenheim (Gurr, 1965, Leonard Hill, London), DAPI (Kuroiwa et al., 1991, Appl. Fluor. Techn. 3 (2): 23–25).

On the level of the cellular pattern, no strieking differences could be found as compared to wild-type root and shoot meristems. All tissue layers were present and were organised as is the case for wild type.

Furthermore, the shape and dimensions of the meristematic cells were comparable with the ones found in wild-type meristems.

However the length of transgenic root meristems are much shorter. The epidermal and cortical cells seem to leave the cell cycle earlier and start elongating in the region where in wild-type roots still divisions occur. In the shoot apical meristem the cells underneath the L1, L2 and L3 layers were larger than cells at the same positions in wild-type shoot meristems. In plants the cell size is often correlated with the basic nuclear DNA content. This demonstrates that the cells in the CKS1At overproducing plants underwent endoreduplication. This is further supported by the observation of large nuclei in the cells of the root meristem of CKS1At overproducing plants.

In conclusion, overproduction of the CKS1At protein did not strikingly affect the global structure and organisation of the meristems itself but accelerated the onset of endoreduplication with cells bigger than normal, containing enlarged nuclei as result. Similar results were obtained in other plant species.

EXAMPLE 9

Generation of a CKS1At-specific antibody

A CKS1At specific antibody was raised by the immunization of rabbits with the CKS1At antigen. The antiserum detected a specific band of approximately 10 kDa in protein extracts prepared from actively dividing cell suspension cells. No signal was observed using the pre-immune serum.

The CKS1At antibody was also able to precipitate CKS1At containing complexes from protein extracts. Protein extracts of actively dividing cells were incubated with the CKS1At antibody (diluted 1/20) for 2 hours on a rotating wheel at 4° C. Subsequently, the extracts were loaded upon 1/30 volume of Sepharose-proteinA beads. After 1 hour incubation at 4° C. the Sepharose-proteinA bound complexes were eluded from the beads by adding SDS PAGE loading buffer and heating for 5 minutes at 95° C. Immunoblotting with the CKS antibody recognized specifically the CKS1At protein in the precipitates. This signal was not observed in precipitates obtained with the use of the pre-immune serum.

EXAMPLE 10

Mutational analysis of the Arabidopsis thaliana CKS1At protein.

CKS1At was shown to bind both CDC2aAt and CDC2bAt in vivo using the two-hybrid system (this application). It has been demonstrated that the last 15 amino-acids of the 87 amino-acids long CKS1At protein are dispensable for this interaction. The recently published structure of the human CDK2 protein in complex with the human CKS1At homologue CKSHs1 helped to identify the amino-acids in the CKS/SUC1 proteins important for interaction with CDKs. Based upon this information the E61 residue of CKS1At was mutated into Q61 by PCR. The consequences of this mutation upon the binding affinity for CDC2aAt and CDC2bAt were tested with the use of a two-hybrid system utilizing the his3 gene as reporter gene. The coding region of both the wild type CKS1At and the mutated CKS1At.Q61 gene was cloned in frame with the GAL4 activation domain in the pGAD424 vector, resulting in the pGADCKS and pGADCKS.Q61 respectively. These vectors were used to cotransform the HF7c yeast cells with pGBTCDC2A or pGBTCDC2B. The pGBTCDC2A and pGBTCDC2B vectors encode for a fusion protein between the GAL4 DNA-binding domain and CDC2aAt or CDC2bAt respectively. The transformants were plated on selective medium in the absence of histidine to test the interactions between CKS1At and CKS1At.Q61 with CDC2aAt and CDC2bAt. Transformants were also streaked on medium containing 10, 20, 40, 80 or 160 mM 3-amino-1,2,4-triazole (3-AT). 3-AT acts as a competitive inhibitor of the his3 gene product. Since the strength of interaction between the different partners in the two-hybrid system is correlated with the level of his3 transcription, the resistance towards increasing concentrations of 3-AT reflects an increasing affinity between the different proteins.

Colonies containing the pGADCKS plasmid in combination with pGBTCDC2A or pGBTCDC2B were able to grow on selective medium containing up to 160 mM 3-AT. In contrast, yeast cells harboring the pGADCKS.Q61 plasmid in combination with pGBTCDC2A grew in the absence of histidine, but growth was completely inhibited in the presence of 10 mM 3-AT, demonstrating that the interaction between CKS1At and CDC2aAt was strongly impaired upon the substitution of the E61 residue. Cotransformants containing pGADCKS.Q61 and pGBTCDC2B were even unable to grow on medium lacking histidine. These results pinpoint the E61 residue in CKS1At as an important amino-acid in CKS1At for the interaction with CDKs.

It has been shown that the induced expression of the wild type CKS1At gene in S. pombe caused cells to arrest in the G2 interphase, displaying an elongated phenotype and growth inhibition (this application). The effects of overexpression of CKS1At.Q61 gene was studied by cloning this gene under the control of the thiamine-repressible nmt1 promoter in the pREP3 vector. In contrast to expression of the wild type CKS1At, expression of CKS1At.Q61 caused no cell cycle arrest. Cells revealed a normal cell cycle and phenotype when grown in the absence of thiamine, although western blotting demonstrated that cells showed an equal accumulation of the CKS1At.Q61 protein as cells getting arrested by the overexpression of the wild type CKS1 AT gene. These results demonstrate that the inhibition of cell division seen by CKS1At overexpression must be mediated through its binding with CDKs.

EXAMPLE 11

Translational control of CKS1At in Arabidopsis cell suspension cultures.

With the use of a CKS1At-specific antibody the accumulation of the CKS1At protein was followed on a time-dependent manner in *A. thaliana* cell suspension cultures. Stationary cells were diluted 1/10 in fresh medium and cultivated for 15 days. Every day a sample of cells was collected and frozen for later analysis. Growth curve determination, by measuring the cell mass weight of 50 ml of culture, demonstrated that after dilution a lag phase occurred from approximately 2 days. From day 2 onwards cells show exponential growth until day 6–7, after which the cells entered the stationary phase.

On western blotting a clear CKS1At signal was observed in a 1 day-old culture. Protein levels increased slightly at day 2 and stayed constant until day 4–5. As cells entered the early stationary growth phase the level of CKS1At decreased and was totally absent in the stationary phase. In comparison, the level of the CDC2aAt protein remained constant during the whole cultivation, while the protein levels of CDC2bAt showed an accumulation pattern similar to that of CKS1At.

Surprisingly, the pattern of CKS1At mRNA did not correlate with levels of CKS1At protein. Northern blotting showed low CKS1At expression at day 1. Expression increased at day 2 and remained approximately constant during the rest of the cultivation. High mRNA levels and low protein levels in stationary cells suggest that a specific degradation mechanism is activated in these cells, repressing the accumulation of the CKS1At protein.

EXAMPLE 12

CKS1At associates in vivo with CDC2aAt at the G1/S transition point but not during the G2 phase.

Arabidopsis thaliana cell suspensions were partially synchronized by the addition of aphidicolin to freshly diluted cell suspension cells. After 24 hours the drug was washed away and cells were cultivated in new medium. Samples were collected at several time points and partly used for nuclei preparation, partly for protein extraction. Flow cytometric analysis showed that cells harvested immediately after removal of the drug were predominantly at the G1/S boundary. In contrast, cells harvested 12 hours later showed an accumulation of cells in G2, just before the onset of mitosis (G2/M). Western blotting demonstrated that for both CDC2aAt and CKS1At equal amounts of the proteins were present at both the G1/S and G2 timepoints. The CKS1At containing complexes were precipitated with the use of a CKS1At specific antibody (see example 9 of this application). These complexes were resolved on a SDS PAGE gel and immunoblotted. The presence of CDC2aAt as a component of the immuno-precipitated complexes was verified by probing this blot with a CDC2aAt specific antibody. This antibody detected a specific band of the correct molecular size in the extracts of the G1/S cells. In contrast, no signal was seen in the extracts of the G2 cells. These results demonstrate the presence of a complex formed in vivo between CDC2aAt and CKS1At at G1/S. During the G2, although both proteins are present at the same level as in G1/S, this complex is not formed.

Dominant negative mutants of CDC2b show endoreduplication

EXAMPLE 13

Generation of the mutant CDC2bAt-D161N allele.

The D161 residue in CDC2bAt is essential for binding a co-factor, ATP. A mutation into 161 N renders an inactive CDK. The dominant effect of the CDC2bAt.N161 mutant is related to the observation that the inactive CDK is still capable to bind other regulatory proteins, necessary for CDK activation. This results in a competition between the CDC2b.N161 mutant and wild type CDKs for the same regulatory proteins.

Mutation D161N (which means that at position 161 the Asp residue is replaced by the Asn residue) was introduced in CDC2bAt cDNA with the use of site directed mutagenesis (sequence of CDC2bAt is disclosed in database with accession number X57840). The cDNA was cloned in pUC18 vector to produce the plasmid pCDC2b-20. The site directed mutagenesis was performed according to the following strategy. The whole plasmid was amplified by PCR using two divergent primers, aatttggqtcttggtcgtg and agcaatcttaagaagctctt, the one bearing the mutation being underlined. The PCR conditions used were: 200 ng template, 125 pmol of each primer, 2,5 µl of 10 mM dNTPs and 0,5 U of Pfu polymerase (Stratagene) and 95° C. 1' and 30 cycles of (92° C. 20', Tm 10', 75° C. 5') and then 75° C. 5'. After PCR amplification 10 U of Dpnl were added to the tube (37° C. for 1 hr) to digest the template. The products of the reactions were separated in 1% low melting point agarose and purified from the gel with the use of gelase (Epicenter Technologies) and then resuspended in TE. After a kinasing reaction the fragments were self ligated and transformed into *E.coli* XL1 Blue. The presence of the mutation and the absence of PCR introduced errors in the resulting plasmid pCDC2b-DN were confirmed by sequencing.

EXAMPLE 14

Analysis of CDC2bAt and CDC2bAt-DN expression in *S. pombe*.

The cDNAs (for wild-type CDC2bAt and for dominant negative CDC2bAt as well) were cloned under the control of negative nmt1 promoter and its attenuated derivative T4 in expression vectors pRep3 (Maundrell,1990, J.Biol.Chem, 265,10857–10864) and pRep4l (Basi et al.1993, Gene,123, 131–136) respectively. The nmt1 promoter is repressed while the cells are grown in the presence of thiamine and can be fully induced after 14 h of incubation in thiamine free medium.

Production of pRep3 Constructs pRep3/CDC2bAt

CDC2bAt cDNA was introduced in pRep3 by replacing CDC2aAt cDNA in the pRep3 based plasmid constructed by Hemerly et al.1995, EMBO J.,14,3925–3936 to express CDC2aAt cDNA in fission yeast. The plasmid was first restricted with Ncol, blunted by Mung Bean exonuclease digestion, and finally restricted with Xmal. The CDC2bAt cDNA was then ligated to the vector as Hpal-Xmal fragment from pCDC2b-20, resulting in pRep3/CDC2bAt.

pRep3/CDC2bAt-DN

The CDC2bAt-DN mutation was introduced into pRep3 by replacing the Sall-BamHl fragment of pRep3/CDC2bAt with the respective fragment carrying the mutation from pCDC2b-DN. The result is pRep3/CDC2bAt-DN.

Production of pRep41 Constructs pRep41/CDC2bAt

CDC2bAt cDNA was ligated as Kpnl (blunted)-BamHl fragment into pRep41opened with Ndel (filled in) and BamHl, resulting in pRep41/CDC2bAt.

pRep41/CDC2bAt-DN

The CDC2bAt-DN mutation was cloned by replacing the Sall-BamHl fragment of the construct above with the respective fragment carrying the mutation. The result is pRep41/CDC2bAt-DN.

Because the pRep3 vector gave a basal expression level in the non-induced conditions, most analyses were done with the pRep41constructs. In general, however, both vectors gave similar results.

Effect of CDC2bAt and CDC2bAt-DN on Cell-cycle Progression in Yeast

The described above expression plasmids were introduced into the yeast strain CDC2-33 leu1-32 h-s (Nurse, 1976, Mol.Gen.Genet.,146, 167–178). Yeast cells were grown first for 24 h in non-inductive conditions (in the presence of 5 μg/ml thiamine) at 25° C. till mid exponential growth phase. Subsequently the thiamine was washed out of the medium and cells were cultivated for 38 h. Samples were harvested after 0 h, 16 h, 20 h, 24 h, 27 h and 38 h after removal of the thiamine. The samples were used for cell number determination, staining of nuclei with the DNA binding fluorochrome DAPI and flow cytometry as described in Sazer and Sherwood et al.(1990,J.Cell.Sci.,97, 509–516). A Becton-Dickinson FACScan was used for flow cytometry. Cells were viewed with a Zeiss Axioscokop microscope. Analysis of the growth curves indicated that cell division was strongly inhibited 6 h after full induction of the promoter for all the constructs tested. Microscopic analysis revealed that upon the expression of CDC2bAt, cells became elongated, characteristic of continued growth in the absence of cell division, and staining with DAPI showed interphase nuclei. Flow cytometric analysis indicated that most of the cells over-expressing CDC2bAt had a 2C DNA content pointing to the arrest in G2 phase of the cell cycle. Similarly over-expression of CDC2bAt-DN in S. pombe also leads to a tight cell-cycle arrest with highly elongated cells. However analysis of DAPI stained cells provided clear evidence for the occurrence of endoreduplication—the majority of cells contained over-sized nuclei and, at later time points, a subpopulation of cells developed grossly swollen nuclei that distended the yeast cell wall.

Determination of the Intrinsic Kinase Activity Associated with the Arabidopsis CDKs Upon Their Over-expression in S. pombe The intrinsic histone H1 kinase activity associated with CDC2bAt and CDC2bAt-DN was determined in protein extracts prepared from S. pombe strain CDC2-L7 leu1-32 h-, which was reported to have negligible CDC2 kinase activity at 37° C. (Moreno et al., 1989, Cell, 58, 361–372). The strains transformed with pRep41/CDC2bAt and pRep41/CDC2bAt-DN were grown in medium without thiamine for 16 hours at 25° C. to induce the nmt1 promoter, while control cultures were grown in the same conditions but in presence of 5 μg/ml thiamine. For H1 kinase assay extracts were made using the HB 15 buffer (Moreno et al. 1989, 1991, Methods Enzymol., 194,795–823), spun at 4 C. in a microfuge for 15', before assaying the concentration of the supernatant and adjusting the sample volume to give an uniform concentration. Kinase assay in the total protein extract was performed at the restrictive temperature 37° C. according to Moreno et al (1989). Neither CDC2bAt nor CDC2bAt-DN showed any detectable kinase activity upon overexpression in the CDC2-L7.

Determination of the Total Histone H1 Kinase Activity in CDC2-33 Background

To correlate the described above alterations in the cell cycle with changes in CDK activity the total histone Hi kinase activity was analysed in the same strains which were used for the cytological studies. The assays were performed at the permissive temperature 25° C. in protein extracts prepared from S. pombe CDC2-33 strain transformed with pRep41/CDC2bAt and pRep41/CDC2bAt-DN which have been grown for 16 h in the inducing conditions (no thiamine). The time point chosen corresponds to 2 h after full induction of the promoter and one generation time before the first changes to the cell division were observed. The protein extracts were prepared as described above and total histone H1 kinase assays were performed with CDK complexes purified from total yeast extract by p13$^{SUC1}$ affinity chromatography according to Azzi et al. (1992, Eur.J.Biochem.,203,353–360). Briefly total yeast extract (100 μg) were incubated with 50 μl 50% (v/v) p13$^{SUC1}$-Sepharose beads for 2 h at 40° C. The washed beads were combined with 30 μl kinase buffer containing 1 mg/ml histone H1, 50 μM ATP and 1 μC. of gamma $^{32}$P-ATP. After 15' incubation, samples were separated by SDS PAGE and analysed by phosphorimager (Molecular Dynamics). Over-expression of both CDC2bAt and CDC2bAt-DN in the CDC2-33 strain induced a reduction in the total histone H1 kinase activity, consistently with the observed cell cycle arrest. These results suggest that CDC2bAt alleles though catalytically inactive in yeast cells are still able of binding some cell cycle regulators thus sequestering them from the endogenous CDC2.

EXAMPLE 15

Analysis of CDC2bAt and CDC2bAt-DN expression in tobacco

The plasmid pUCA7-TX, bearing the 'Triple-Op' promoter (Gatz 1992, Plant.J.,2,397404, dubbed Top3 hereafter) in pUC18, was opened with BamHl and Sphl and a fragment BamHl-Sphl containing the nos gene polyadenylation site (polyA$^{nos}$) was ligated to. Then an Xbal linker was inserted in the Sphl site (trimmed off with T4 DNA polymerase) downstream of polyA$^{nos}$ to produce the plasmid pUCA7-TXnosX. This plasmid was opened with BamHl and Kpnl and the fragments containing either CDC2bAt or CDC2bAt-DN cDNAs were cloned to as Kpnl-BamHl fragments between Top3 and polyA$^{nos}$ resulting in the plasmids pTop3CDC2b and pTop3CDC2bDN respectively. The expression cassettes Top3-CDC2bAt-polyA$^{nos}$ and Top3-CDC2bAtDN-polyA$^{nos}$ were transferred as EcoRI(filled in)-Xbal fragments of the above plasmids into the binary vector pGSC1704 (Plant Genetic Systems N.V.) opened with SnaBI and Xbal. The resulting binary plasmids pBinTop3CDC2b and pBinTop3CDC2bDN were checked by Ncol-Xbal digestion and sequenced through the region of the mutation. The binary plasmids were introduced in Nicotiana tabacum cv Petit havana (SR1) plants by the leaf disc protocol (Horsh,1985,Science,227,1229–1231). The level of expression of CDC2b and CDC2bDN in the transgenic lines, 15 for each transformation, was analysed by Western blotting as described above. Of the total 12 lines expressing CDC2b and 13 lines expressing CDC2bDN, two lines from each transformation with the highest levels of expression were selected for further analysis. The two wild-type lines are designated CDC2b-14 and CDC2b-23 whereas the two dominant negative mutant lines are coded CDC2bDN-1 and CDC2bDN-27 respectively. For the determination of kinase activity associated with CDC2b in the transgenic plants, protein extracts from 2 week old in vitro grown plants were prepared as described above and protein complexes were immunoprecipitated from 200 μg of the total protein with the use of an antibody (1/200 dilution) raised against the peptide SAKTALDHPYFDSCDKSQF derived from CDC2bAt. The antibody had been previously shown to specifically recognise also a CDC2bAt-like kinase from tobacco. The histone H1 kinase activity in the precipitated complexes was determined according to Magyar et al. 1993, Plant J.,4,151–161. It was found that overexpression of CDC2bAt did not influence the kinase activity in a detectable way, whereas overexpression of CDC2bDN resulted in a strong reduction of the kinase activity, down to 20% of the control level. When the roots of the transgenic plants were analysed by confocal microscopy, the cells of the plants overexpressing CDC2bDN were found to possess considerably enlarged nuclei, pointing to an increase in the DNA content. The measurement of the nuclei in the root tips produced the average size 49.5 μm for the line CDC2bDN-1 and 37.1 μm for the line CDC2b-23 as compared to 35.2 μm in the control. The DNA content in the transgenic plants was further analysed by flow cytometry (Galbraith et al. 1991, Plant.Physiol.,96,985–989). All the four "CDC2b-indicated" lines analysed showed considerable increase in the nuclear DNA content in the cotyledons compared to the wild-type SRI control (see the table).

| DNA content | COTYLEDONES | | | |
|---|---|---|---|---|
| | 2C | 4C | 8C | 16C |
| SR1 (control) | 93% | 6% | 0.42% | 0.19% |
| CDC2b -14 | 63% | 34% | 0.63% | 2.50% |
| CDC2b -23 | 62% | 33% | 2.70% | 2.30% |
| CDC2b DN-1 | 70% | 24% | 3.60% | 2.10% |
| CDC2b DN-27 | 69% | 27% | 2.20% | 1.60% |

Both in the lines overexpressing CDC2b and the lines expressing the dominant negative mutants of CDC2b, the number of cells in the cotyledones with normal nuclear DNA content (2C) decrease and the percentage of cells with increased nuclear DNA content (from 4C up to 16C) significantly increases. This demonstrates that modulated expression of CDC2b and/or expression of dominant negative mutants of CDC2b clearly modulates the endoreduplication in plants and plant cells.

Similar results are obtained in plant species different from tobacco.

What is claimed is:

1. An isolated and/or recombinant nucleic acid molecule encoding at least a functional part of a CKS1 protein, wherein the isolated and/or recombinant nucleic acid molecule comprises a nucleotide sequence encoding a protein comprising the amino acid sequence as given in SEQ ID NO:3 or 4 or a functional part thereof, or a nucleic acid molecule comprising the nucleotide sequence as given in SEQ ID NO:1 or 2.

2. The nucleic acid molecule of claim 1 which is derived from a plant.

3. The nucleic acid molecule of claim 2, wherein the plant is *Arabidopsis thaliana*.

4. A chimeric gene comprising a nucleic acid molecule of any one of claims 1 to 3 operatively linked to an expression control sequence.

5. A vector comprising a nucleic acid molecule of any one of claims 1 to 3.

6. A host cell comprising a nucleic acid molecule of any one of claims 1 to 3.

7. A method for the production of a transgenic plant or plant cell, said method comprising the introduction of a nucleic acid molecule of any one of claims 1 to 3 into the genome of said plant or plant cell.

8. The method of claim 7 further comprising regenerating a plant from said cell.

9. A transgenic plant cell comprising a nucleic acid molecule of any one of claims 1 to 3.

10. A transgenic plant comprising plant cells of claim 9.

11. Transgenic plant material from a plant of claim 10.

12. Transgenic plant material of claim 11 comprising roots, flowers, fruit, leaves, pollen, seeds, seedlings, or tubers.

13. Transgenic progeny of a plant of claim 10 comprising the isolated and/or recombinant nucleic acid of claim 1.

14. A vector comprising the chimeric gene of claim 4.

15. A host cell comprising a chimeric gene of claim 4.

16. A host cell comprising a vector of claim 5.

17. A host cell comprising a vector of claim 14.

18. A method for the production of a transgenic plant or plant cell, said method comprising the introduction of a chimeric gene of claim 4 into the genome of said plant or plant cell.

19. A method for the production of a transgenic plant or plant cell, said method comprising the introduction of a vector of claim 5 into the genome of said plant or plant cell.

20. A method for the production of a transgenic plant or plant cell, said method comprising the introduction of a vector of claim 14 into the genome of said plant or plant cell.

21. A transgenic plant cell comprising a chimeric gene of claim 4.

22. A transgenic plant cell comprising a vector of claim 5.

\* \* \* \* \*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 454 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (vi) ORIGINAL SOURCE:
      (A) ORGANISM: Arabidopsis thaliana (ix) FEATURE:
      (A) NAME/KEY: CDS
      (B) LOCATION:15..276

(xi) SEQUENCE DESCRIPTION: SEQ ID NO: 1:

```
CCTCTGAGAG AGAA ATG GGT CAG ATC CAA TAC TCC GAG AAA TAC TTC GAT           50
              Met Gly Gln Ile Gln Tyr Ser Glu Lys Tyr Phe Asp
                1               5                      10

GAC ACT TTC GAA TAC AGG CAC GTC GTT CTT CCT CCT GAA GTC GCT AAA           98
Asp Thr Phe Glu Tyr Arg His Val Val Leu Pro Pro Glu Val Ala Lys
         15                  20                  25

CTT CTT CCA AAG AAT CGT CTT CTC TCC GAA AAC GAA TGG CGA GCG ATA          146
Leu Leu Pro Lys Asn Arg Leu Leu Ser Glu Asn Glu Trp Arg Ala Ile
     30                  35                  40

GGA GTG CAG CAA AGC CGC GGA TGG GTA CAT TAC GCG GTT CAT CGA CCT          194
Gly Val Gln Gln Ser Arg Gly Trp Val His Tyr Ala Val His Arg Pro
 45                  50                  55                  60

GAG CCG CAC ATA ATG CTA TTC AGG AGG CCT CTT AAC TAT CAG CAG CAG          242
Glu Pro His Ile Met Leu Phe Arg Arg Pro Leu Asn Tyr Gln Gln Gln
                 65                  70                  75

CAG GAG AAT CAA GCT CAG AAC ATG CTT GTT AAG T GAATCATTAT                 286
```

```
                 Gln Glu Asn Gln Ala Gln Asn Met Leu Val Lys
                         80                  85

CATCACCTGA GTAAGAATGT TATATGCAAC AATTCTATGA GTATTGGTTT ATGTTTCTTG      346

TAAACATGGT TTGAATCTTT GTGGTTATGG ATGAATATGT GAGAGTTGGT TTGTTGAACA      406

ACTTCTATGT AATGTTAGTC TTGGTTCTAA TGTCATCTTC TGCTTCTC                   454

(2) INFORMATION FOR SEQ ID NO: 2:

(i) SEQUENCE CHARACTERISTICS:
        (A) LENGTH: 696 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Arabidopsis thaliana (xi) SEQUENCE DESCRIPTION: SEQ ID NO: 2:

ATGGGTCAGA TCCAATACTC CGAGAAATAC TTCGATGACA CTTTCGAATA CAGGTAAAGC       60

TCTTCAATCT CGCTTCTTCT TCCTCCAATT TTCACTCTCA CTTCTCTAAT CGTAATCGAT      120

CGATACAGGC ACGTCGTTCT TCCTCCTGAA GTCGCTAAAC TTCTTCCAAA GAATCGTCTT      180

CTCTCCGAAG TAAGTTTTTT TCCGCATTGT TCTCTGATTT CTGATTCTAA ATCCTTCGAT      240

TAGATCATCG AAGACTATGA AAATTTGTTG CTCTTAAGAA ATTAAGTTTG GAAAAATCG       300

AAAAAGAGAT CGTTTAGGTT TAGGATTTGA ATCTTTGCTC TGAATCCAAA TTGCAACTGT      360

TACGATTTTG AATCTTTGCT TTGGGATTTT GTAAGGTTTA GTGATAAAGA GATTTTAGAC      420

ATTTGTGTTG TGCAATCTCT TCAATGTTGT ATTGATTGGT GGTGATGGTA AAAATGTTTG      480

GAATTTCGAA GAACGAATGG CGAGCGATAG GAGTGCAGCA AAGCCGCGGA TGGGTACATT      540

ACGCGGTTCA TCGACCTGAG CCGCACATAA TGCTATTCAG GAGGCCTCTT AACTATCAGC      600

AGCAGCAGGA GAATCAAGCT CAGAACATGC TTGTTAAGTG AATCATTATC ATCACCTGAG      660

TAAGAATGTT ATATGCAACA GATCTATGAG TATTGG                                696

(2) INFORMATION FOR SEQ ID NO: 3:

(i) SEQUENCE CHARACTERISTICS:
        (A) LENGTH: 87 amino acids
        (B) TYPE: amino acid
        (C) STRANDEDNESS: <Unknown>
        (D) TOPOLOGY: linear (ii) MOLECULE TYPE: peptide (vi) ORIGINAL SOURCE:
        (A) ORGANISM: Arabidopsis thaliana (ix) FEATURE:
        (A) NAME/KEY: Peptide
        (B) LOCATION:1

(xi) SEQUENCE DESCRIPTION: SEQ ID NO: 3:

Met Gly Gln Ile Gln Tyr Ser Glu Lys Tyr Phe Asp Asp Thr Phe Gl
1               5                  10                  15

Tyr Arg His Val Val Leu Pro Pro Glu Val Ala Lys Leu Leu Pro Ly
                20                  25                  30

Asn Arg Leu Leu Ser Glu Asn Glu Trp Arg Ala Ile Gly Val Gln Gl
            35                  40                  45
```

```
Ser Arg Gly Trp Val His Tyr Ala Val His Arg Pro Glu Pro His Il
    50                  55                  60

Met Leu Phe Arg Arg Pro Leu Asn Tyr Gln Gln Gln Glu Asn Gl
65                  70                  75                  80

Ala Gln Asn Met Leu Val Lys
                85
```

(2) INFORMATION FOR SEQ ID NO: 4:

(i) SEQUENCE CHARACTERISTICS:
       (A) LENGTH: 72 amino acids
       (B) TYPE: amino acid
       (C) STRANDEDNESS: <Unknown>
       (D) TOPOLOGY: linear (ii) MOLECULE TYPE: peptide (vi) ORIGINAL SOURCE:
        (A) ORGANISM: Arabidopsis thaliana (ix) FEATURE:
        (A) NAME/KEY: Peptide
        (B) LOCATION:1

(xi) SEQUENCE DESCRIPTION: SEQ ID NO: 4:

```
Met Gly Gln Ile Gln Tyr Ser Glu Lys Tyr Phe Asp Asp Thr Phe Gl
1               5                   10                  15

Tyr Arg His Val Val Leu Pro Pro Glu Val Ala Lys Leu Leu Pro Ly
                20                  25                  30

Asn Arg Leu Leu Ser Glu Asn Glu Trp Arg Ala Ile Gly Val Gln Gl
            35                  40                  45

Ser Arg Gly Trp Val His Tyr Ala Val His Arg Pro Glu Pro His Il
    50                  55                  60

Met Leu Phe Arg Arg Pro Leu Asn
65                  70
```